United States Patent [19]

Le Blanc, Jr. et al.

[11] 4,443,560

[45] Apr. 17, 1984

[54] ADIABATICALLY REFORMING A REFORMED GAS FOR PRODUCING METHANOL

[75] Inventors: Joseph R. Le Blanc, Jr.; Dewey O. Moore, both of Houston; Robert V. Schneider, III, Missouri City, all of Tex.

[73] Assignee: The M. W. Kellogg Company, Houston, Tex.

[21] Appl. No.: 402,468

[22] Filed: Jul. 28, 1982

[51] Int. Cl.$^3$ .................. C07C 27/06; C07C 31/04
[52] U.S. Cl. .................................. 518/703; 518/704
[58] Field of Search .............................. 518/703, 704

[56] References Cited

U.S. PATENT DOCUMENTS 3,598,527  8/1971  Quartulli et al. .................. 518/704
4,277,416  7/1981  Grant .................................. 518/703

Primary Examiner—Howard T. Mars

[57] ABSTRACT

The present invention is an improvement to a process for producing methanol which uses both steam reforming and partial oxidation by adiabatically reforming with substantially pure oxygen the reformed gas to produce the maximum amount of hydrogen for the synthesis of methanol.

1 Claim, 1 Drawing Figure

ADIABATICALLY REFORMING A REFORMED GAS FOR PRODUCING METHANOL

BACKGROUND OF THE INVENTION

This invention relates to a process for producing methanol which uses steam reforming, e.g. steam reforming natural gas, and partial oxidation, e.g. partial oxidation of coal, as sources of the methanol synthesis gas. More specifically, the present invention is an improvement to a process for producing methanol which uses both steam reforming and partial oxidation by adiabatically reforming with substantially pure oxygen the reformed gas to produce the maximum amount of hydrogen for the synthesis of methanol.

The prior art discloses methods for producing methanol using natural gas as the hydrocarbon feed and other methods using coal as the hydrocarbon feed.

BACKGROUND REFERENCES

The following references are incorporated into the disclosure of this patent by reference:

1. Kirk-Othmer, ENCYCLOPEDIA OF CHEMICAL TECHNOLOGY, 3rd Ed., Vol. 15, pp. 398–415, "Methanol".
2. Kirk-Othmer, ENCYCLOPEDIA OF CHEMICAL TECHNOLOGY, 3rd Ed., Vol. 6, pp. 224–377, "Coal" and "Coal Conversion Processes".
3. Kirk-Othmer, ENCYCLOPEDIA OF CHEMICAL TECHNOLOGY, 2nd Ed., Vol. 10, pp. 353–442, "Gas, Manufactured".
4. U.S. Pat. No. 4,277,416 which discloses a single methanol plant which is fed by clean syn-gas from coal gasification and syn-gas from natural gas.

The following references are included as being of interest:

| U.S. Pat. Nos. | |
|---|---|
| 3,501,516 | 3,993,475 |
| 3,920,717 | 4,065,483 |
| 3,940,428 | 4,076,761 |
| 3,962,300 | 4,203,915 |
| 3,972,958 | 4,219,492 |
| | 4,238,403 |

SUMMARY OF THE INVENTION

The present invention is an improvement to a process for producing methanol which uses both steam reforming and partial oxidation by adiabatically reforming with substantially pure oxygen the reformed gas to produce the maximum amount of hydrogen for the synthesis of methanol.

More specifically, the present invention is directed to a process for producing methanol which comprises converting a $C_1$ to $C_4$ gas by steam reforming into a reformed gas mixture comprising hydrogen, methane and carbon oxides; converting a heavy carbonaceous material by partial oxidation using substantially pure oxygen into a raw gas comprising hydrogen, carbon monoxide, carbon dioxide, other acid gases, nitrogen and argon; removing from said raw gas the other acid gases and trace compounds of sulfur to produce a clean syn-gas; and reacting said reformed gas and said clean syn-gas in a methanol plant, the improvement which comprises:

adiabatically reforming said reformed gas prior to reacting said reformed gas and said clean syn-gas in said methanol plant.

DETAILED DESCRIPTION OF THE PREFERRED EMBODIMENTS

Figure 1:
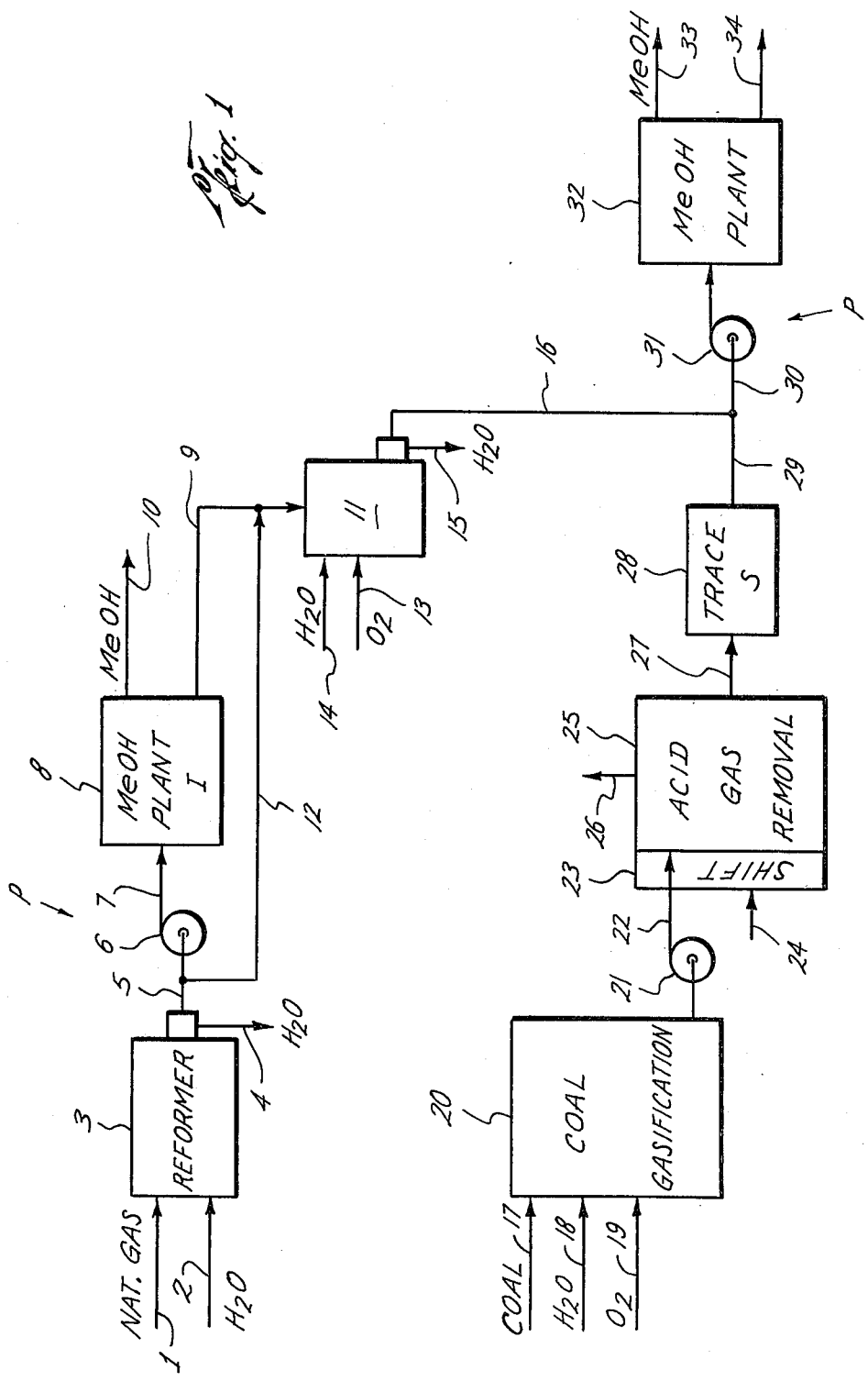
FIG. 1 is a block flow diagram of the present invention.

Normally, methanol is produced by the catalytic conversion of a methanol synthesis gas mixture containing hydrogen and carbon oxides at elevated pressure. The catalytic conversion in which a highly selective copper-based catalyst is employed may be represented by the following chemical equations:

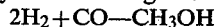
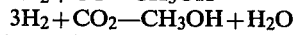

$$2H_2 + CO \rightarrow CH_3OH$$
$$3H_2 + CO_2 \rightarrow CH_3OH + H_2O$$

The methanol synthesis gas mixture is usually prepared by steam reforming a $C_1$ to $C_4$ gas, such as natural gas, $C_1$ to $C_4$ hydrocarbons or mixtures thereof or a refinery gas stream having a high $C_1$ to $C_4$ content. In a methanol process where only steam reforming is used to produce the methanol synthesis gas mixture however, the synthesis gas mixture thus produced has an excess of hydrogen for the stoichiometry of the methanol synthesis reaction. Therefore to achieve a more optimum hydrogen/carbon oxides balance, carbon dioxide, if available, is often added to the methanol synthesis gas. In the process of the present invention, all the hydrogen produced by steam reforming of the $C_1$ to $C_4$ gas is used to produce methanol and does not require the added unit operation of adding carbon dioxide.

The supply of methanol synthesis gas may be alternately derived from other fossil fuel sources, i.e. heavy carbonaceous materials such as coal, coke, shale, and petroleum residues. A synthesis gas suitable for use in the production of methanol from such heavy carbonaceous materials can be obtained by high temperature partial oxidation using essentially pure oxygen. The partial oxidation of coal or coal gasification, such as processes using a Shell gasifier or a Texaco gasifier, are known in the art. However, a methanol process using a synthesis gas derived from such heavy carbonaceous materials alone is very expensive on the scale required for reasonably sized methanol plants. Further, the reliability of the partial oxidation process for on-stream performance is much less than for steam reforming.

As the availability of natural gas decreases or as the gas becomes more expensive, an alternate source of fossil fuel becomes necessary for the production of methanol synthesis gas. According to the process of the present invention, the advantages of the steam reforming process are maintained while integrating a second source of methanol synthesis gas produced by partial oxidation. Further, according to the process of the present invention, the maximum amount of hydrogen is produced from the $C_1$ to $C_4$ gas which reduces the size of the more expensive partial oxidation unit operation. Another advantage of the present invention is that the existing methanol plant now using steam reforming of natural gas without supplemental feed of carbon dioxide may be modified to expand its capacity.

Referring to FIG. 1, natural gas is introduced by line 1 together with steam by line 2 into a steam reformer 3. Steam reforming is a conventional unit operation and known in the art. The conventional steam reformer is a furnace having a series of tubes filled with a nickel or treated nickel catalyst over which the natural gas passes and is converted into a reformed gas mixture. The mixture comprises hydrogen, carbon oxides, small amounts of unconverted hydrocarbons, mainly methane, and the inert gases nitrogen and argon. This reformed gas mixture is removed from the steam reformer 3 and passed through a series of heat exchangers for heat recovery with the condensed water removed by line 4. The dry mixture of gases is then passed by line 5 to a gas compressor 6. In one embodiment of the present invention, the reformed gas mixture is the feed to a pre-existing methanol plant. There, the compressed gases pass through line 7 to methanol plant 8. For the purposes of this patent, the methanol plant 8 is inclusive of a reactor or reactors which contain the methanol catalyst, the recycle system which recycles the unconverted gases through the reactor since only a percentage of the gas is converted to methanol on any pass through the reactor and all associated equipment to produce the crude methanol. Thus the term "methanol plant" as used herein is inclusive of all necessary equipment to produce the crude methanol. Usually included is purification equipment to produce high purity methanol such as a distillation system.

The methanol plant 8 may be represented by a low pressure methanol plant operating at synthesis pressures of 50-100 atmospheres and employing an ICI, Lurgi, or other copper catalyst based methanol process. The low pressure synthesis operating with a copper-based catalyst is generally in the temperature range of 240°-270° C. However, the specific reactor, catalyst or conditions are not material to the present invention and such are known in the art.

A purge is taken from methanol plant 8 by line 9. This purge is taken from the recycle loop to the reactor or reactors normally, to rid the system of the inert gases and excess hydrogen. The methanol plant 8 also produces a first methanol stream 10.

According to the present invention, the methane which is in the reformed gas mixture is adiabatically reformed to produce additional hydrogen. The unit operation is secondary reforming where the reformed gas mixture is contacted with steam and oxygen in the presence of a steam reforming catalyst. The steam reforming catalysts which may be employed in secondary reforming are nickel, nickel oxide, chromia, molybdenum, mixtures thereof, etc. The mixed steam and oxygen, substantially pure oxygen obtained in an air separation plant is usually employed, and reformed gas mixture is passed through a secondary reformer at pressures between 20 and 70 atmospheres and at an exit temperature between 800° C. and 1100° C. The hydrocarbons, primarily methane, are reacted to produce hydrogen, carbon oxides and water. The production of additional hydrogen from the reformed gas mixture, whether it is passed through a first or pre-existing methanol plant or passes directly to the secondary reformer, enables the secondary reforming effluent to be used with a syn-gas stream produced by partial oxidation to feed a methanol plant as will be described in more detail hereinafter.

Referring again to FIG. 1, the purge steam 9 is the reformed gas mixture introduced to secondary reformer 11. Alternatively, if a pre-existing methanol plant using a $C_1$ to $C_4$ gas feed is not present or a first methanol plant is not desired, the reformed gas mixture is passed directly to secondary reformer 11 by line 12. Substantially pure oxygen added by line 13 and steam added by line 14 are introduced to the secondary reformer 11.

The temperatures at the inlet may range from 540° C. to 825° C. with theoretical maximum flame temperatures of about 1250° to 1450° C. within the secondary reformer 11.

The effluent from the secondary reformer 11 is passed through a heat exchanger and water condensed and removed by line 15. The essentially dry gas is then passed by line 16 to be combined with a syn-gas stream produced by partial oxidation.

A second source of hydrocarbon is a heavy carbonaceous material, preferably coal. Coal or coal plus water is fed by line 17, steam by line 18 and oxygen by line 19 to a coal gasifier 20. The gasifier is preferably a high temperature gasifier known in the art, i.e. a Shell gasifier, a Shell-Koppers gasifier or a Texaco gasifier. In these gasifiers a raw gas is produced. The composition of the raw gas will depend on the specific coal and gasification technique employed; however, the gas is mostly carbon monoxide and hydrogen. The raw gas from the gasifier 20 will also contain some carbon dioxide and other acid gases besides the inert gases argon and nitrogen. For the purposes of this patent, the term "other acid gases" are the other acid gases besides carbon dioxide, such as the sulfur containing gases, i.e. $H_2S$ and COS, and cyanides. The other acid gases are all more selectively absorbed than the carbon dioxide. The raw gas is passed through optional compressor 21 and line 22 into a high temperature shift unit 23. The shift is carried out in a conventional manner by the addition of steam through line 24 which when passed over the known sulfur-resistant catalysts converts the carbon monoxide to carbon dioxide and hydrogen by the following well known shift reaction:

$$CO + H_2O \rightarrow H_2 + CO_2$$

This unit operation is dependent on the relative amount of the reformed gas and clean syn-gas employed in the process of the present invention so that all or a portion or none of the raw gas from gasifier 20 may pass through the high temperature shift 23.

Following the high temperature shift unit 23 is an acid gas removal system 25. The acid gas removal system 25 may use any of the well known absorbents, i.e. methanol, polyethylene glycol dimethyl ether, monoethanol amine (MEA)—diethanol amine (DEA), for acid gases and is operated to selectively absorb the other acid gases with some removal of carbon dioxide. The acid gases are usually removed by contacting or scrubbing the raw gas from the gasifier 20 with the absorbent in an absorption tower. The rich absorbent solution, i.e. the other acid gases containing absorbent, can be readily regenerated for reuse. The regeneration may be carried out in a stripper column where the rich absorbent solution is heated and/or reduced in pressure which separates the small amount of carbon dioxide and other acid gases from the absorbent. The small amount of carbon dioxide and other acid gases are removed from the acid gas removal system 25 by line 26.

The scrubbed gas is removed by line 27 and passed through a guard chamber 28 containing zinc oxide to remove any trace sulfur in the gases. Since sulfur is a poison to the methanol catalysts, the guard chamber 28 is a precautionary operation and other alternatives may be employed.

According to the present invention, the clean syn-gas, a gas which by its normal composition would not be a desirable syn-gas for methanol, from the guard chamber 28 is removed by line 29 and together with the gas in line 16 from the secondary reformer 11 is introduced by line 30 to a compressor 31 for introduction to a methanol plane 32 at the desired operating pressure. A crude methanol stream 33 and a purge stream 34 are removed from methanol plant 32.

For a better understanding of the present invention, reference is made to the following specific example, which makes reference to the drawing.

6957 pound moles/hour (#mol/hr) of desulfurized natural gas, line 1 and 25609 #mol/hr of steam, line 2, are fed to a conventional steam reformer 3. The reforming is carried out over conventional nickel catalyst, and after waste heat recovery and condensing 16433 #mol/hr of water, line 4, essentially dry reformed gas is available at 17.3 atmospheres (255 psia). The reformed gas, line 5, consists of 29364 #mol/hr of gas with a composition of 73.38 mol% $H_2$; 13.61 mol% CO; 8.98 mol% $CO_2$; 3.99 mol% $CH_4$ and 0.04 mol% $N_2+A$. The reformed gas, line 5, is compressed by compressor 6 to 80 atmospheres (1176 psia) to provide feed gas, line 7, to a first methanol plant 8. Using a conventional ICI methanol catalyst and low pressure (50–100 atmospheres) a crude methanol stream, line 10, consisting of 6314 #mol/hr of pure methanol together with 2489 #mol/hr of water and small amounts of other impurities is produced. The crude methanol stream 10 can be further purified by conventional distillation as desired.

A purge stream, line 9, is taken out of the first methanol plant 8 at about 80 atmospheres (1176 psia) to remove inerts in the recycle to the reactors. The inerts are methane, nitrogen and argon. The purge stream, line 9, contains 7933 #mol/hr gas having a composition: 81.07 mol% $H_2$; 2.14 mol% CO; 1.86 mol% $CO_2$; 14.79 mol% $CH_4$; and 0.14 mol% $N_2+A$ which is introduced into secondary reformer 11. Also introduced is 1031 #mol/hr of substantially pure oxygen, line 13, and 8797 #mol/hr of steam, line 14. The pressure in the secondary reformer 11 is about 31.6 atmospheres (465 psia) with an exit temperature of about 982° C. (1799° F.). The water, 9269 #mol/hr, is condensed from the secondary reformer effluent, line 15 and 9718 #mol/hr of gas with a composition 84.30 mol% $H_2$; 8.86 mol% CO; 6.03 mol% $CO_2$; 0.45 mol% $CH_4$; 0.11 mol% $N_2+A$ and 0.25 mol% $H_2O$, is recovered.

In addition, 54656 #/hr of dried coal (Illinois No. 6), line 17, is introduced with 196 #mol/hr of water or steam, line 18, and 1223 #mol/hr of pure oxygen, line 19, to a gasifier 20. After waste heat recovery to raise steam and removal of 7007 #/hr of wet ash and slag, 4542 #mol/hr of raw gas is produced, with a composition: 32.08 mol% $H_2$; 65.02 mol% CO; 0.79 mol% $CO_2$; 0.70 mol% $N_2+A$; and 1.41 mol% other acid gases, at a pressure of about 31.6 atmospheres (465 psia). The other acid gases are various sulfur and cyanide compounds. The raw gas is passed over a high temperature sulfur resistant shift catalyst in shift unit 23 to provide a feed gas to a conventional acid gas removal system 25 which removes 64 #mol/hr of other acid gases and some small amount of carbon dioxide, line 26. The sulfur compounds in the other acid gas are poisons to the methanol synthesis catalysts. The clean gas, line 27, is passed over a zinc oxide (ZnO) guard bed in guard chamber 28 for trace sulfur compound removal. The clean syn-gas, line 29, consists of 4656 #mol/hr of gas with a composition: 35.90 mol% $H_2$; 59.62 mol% CO; 4.60 mol% $CO_2$; and 0.69 mol% $N_2+A$. This clean syn-gas, line 29, is mixed with the adiabatically reformed purge gas stream from the first methanol plant, line 16, to give a total syn-gas, line 30, of 14374 #mol/hr, with a composition: 68.36 mol% $H_2$; 25.30 mol% CO; 5.56 mol% $CO_2$; 0.31 mol % $CH_4$; 0.30 mol% $N_2+A$; and 0.17 mol% $H_2O$, which is introduced to the second methanol plant 32 at a pressure about 80 atmospheres (1176 psia) via compressor 31.

The second methanol plant produces a crude methanol stream, line 33, consisting of 4304 #mol/hr methanol, 760 #mol/hr $H_2O$ plus small amounts of impurities. A purge stream is produced, line 34, with 702 #mol/hr of gas having a composition: 68.09 mol% $H_2$; 10.40 mol% CO; 8.55 mol% $CO_2$; 6.12 mol% $N_2+A$; 6.27 mol% $CH_4$ and 0.57 mol% $H_2O$, which may be used as fuel.

The total pure methanol production from the integrated plants of the present invention is the sum of the pure methanol of the two crude product streams, line 10 and 33, namely 10618 #mol/hr pure methanol.

The advantage of the present invention is that, by using adiabatic reforming, better utilization of raw material feed stock is obtained for the same methanol capacity. The example shows a 5% savings in $C_1$ to $C_4$ gas and about 23% in the coal feed stocks utilization compared to the same configuration without the secondary reforming of the present invention to produce the same amount of methanol.

Further, the integrated plants of the present invention take advantage of the on stream reliability of the processes which produce the methanol synthesis gas. The steam reforming process is better than 95% reliable whereas the coal gasification process is just over 80%. Thus, when the clean syn-gas from the coal gasification process is shut down, the first methanol plant of the present invention is not affected and may continue to operate under design conditions.

Still further, the integrated plants of the present invention may be used with a steam reforming process and a coal gasification process where no shift reaction is carried out on the raw gas from the coal gasifier. The advantage is the elimination of an entire process unit and in addition a smaller acid gas removal system.

In summary, the present invention uses to a maximum advantage the steam reforming process and a partial oxidation process of converting a heavy carbonaceous material to produce synthesis gas which taken individually are not an optimum synthesis gas for methanol, and integrated the operations are such that an improved process for producing methanol is achieved.

We claim:

1. In a process for producing methanol and purge gas in a first methanol plant and a second methanol plant wherein methanol from the first methanol plant is synthesized from a reformed gas mixture comprising hydrogen, methane, and carbon oxides produced by steam reforming $C_1$ to $C_4$ hydrocarbons and wherein methanol from the second methanol plant is synthesized from a clean synthesis gas comprising hydrogen and carbon monoxide produced by partial oxidation with substantially pure oxygen of a heavy carbonaceous material, the improvement which comprises:
   (a) recovering purge gas containing hydrogen, methane, and carbon monoxide from the first methanol plant;
   (b) adiabatically reforming the recovered purge gas to produce adiabatically reformed purge gas; and
   (c) mixing adiabatically reformed purge gas with clean synthesis gas from the heavy carbonaceous material partial oxidation step and introducing the resulting mixed gas to the second methanol plant.

* * * * *